United States Patent [19]

Rutledge

[11] 4,070,383
[45] Jan. 24, 1978

[54] OXIDATIVE COUPLING OF PHENOLS AND NAPHTHOLS

[75] Inventor: Thomas F. Rutledge, Wilmington, Del.

[73] Assignee: ICI Americas Inc., Wilmington, Del.

[21] Appl. No.: 655,104

[22] Filed: Feb. 4, 1976

Related U.S. Application Data

[63] Continuation-in-part of Ser. No. 550,445, Feb. 18, 1975, abandoned, which is a continuation-in-part of Ser. No. 499,826, Aug. 23, 1974, abandoned.

[51] Int. Cl.$^2$ .................. C07C 37/00; C07C 39/12; C07C 39/16; C07C 45/16; C07C 49/62; C07C 49/72

[52] U.S. Cl. .......................... 260/396 N; 252/429 R; 252/430; 260/47 ET; 260/613 R; 260/619 B; 260/619 F; 260/620

[58] Field of Search .......... 260/396 N, 47 ET, 619 F, 260/613 R, 620, 619 B

[56] References Cited

U.S. PATENT DOCUMENTS

| | | | |
|---|---|---|---|
| 3,306,874 | 2/1967 | Hay | 260/396 N |
| 3,306,875 | 2/1967 | Hay | 260/396 N |

FOREIGN PATENT DOCUMENTS

| | | | |
|---|---|---|---|
| 4,727,216 | 7/1972 | Japan | 260/396 N |

*Primary Examiner*—Vivian Garner

[57] ABSTRACT

Self-condensation products obtained by the coupling of alkylphenols, alkoxyphenols or naphthols are prepared by contacting an aqueous mixture of the phenol or naphthol with oxygen or an oxygen-containing gas in the presence of a catalyst system comprising
 a. a copper compound,
 b. an anionic surfactant, and
 c. an alkaline material.

23 Claims, No Drawings

OXIDATIVE COUPLING OF PHENOLS AND NAPHTHOLS

BACKGROUND OF THE INVENTION

This application is a continuation-in-part of application Ser. No. 550,445 filed Feb. 18, 1975, which is a continuation-in-part of application Ser. No. 499,826 filed Aug. 23, 1974, both abandoned.

FIELD OF THE INVENTION

The present invention relates generally to an improved process for preparing self-condensation products, such as diphenoquinones, biphenols, dinaphthenoquinones and binaphthols from alkylphenols, alkoxyphenols and naphthols and to a catalyst composition for use in said process. More particularly, the invention relates to a method of preparing condensation products of alkylphenols, alkoxyphenols, or 1-naphthols by contacting an aqueous mixture of the phenol or naphthol with oxygen or an oxygen-containing gas in the presence of a catalyst system comprising a. a copper compound,
b. an anionic surfactant, and
c. an alkaline material.

DESCRIPTION OF THE PRIOR ART

It is well known in the art that substituted phenols can be oxidized to yield self-condensation products, including diphenoquinones, biphenols and polyphenoxy ethers. The procedure employed in the preparation of these derivatives is generally referred to as the oxidative coupling of phenols.

The self-condensation products resulting from these oxidative coupling reactions can be catagorized as either the result of carbon-carbon coupling or carbon-oxygen coupling of said phenols. Diphenoquinones and biphenols are prepared by carbon-carbon coupling in accordance with the following general reactions depending upon the reactive sites available in the phenol employed.

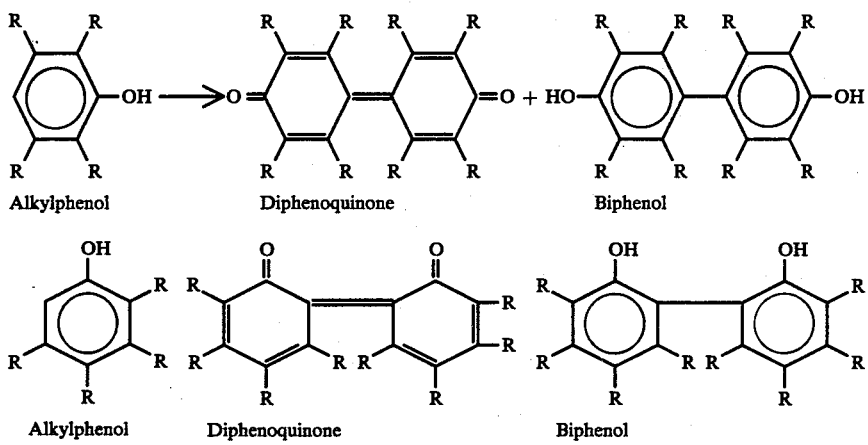

wherein R is either hydrogen, alkyl, alkoxy, or another substituent all of which are well known in the art.

Similarly, polyphenoxy ethers are prepared by carbon-oxygen coupling in accordance with the reactions such as the following general reaction:

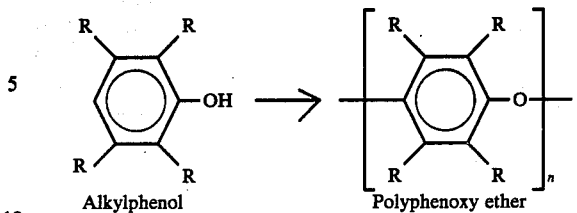

wherein R is as defined above and $n$ is an integer.

A variety of materials, including metals and various salts and complexes thereof, have previously been disclosed as useful in promoting the oxidative coupling of alkylphenols. Thus, U.S. Pat. No. 2,785,188 issued to Coe, discloses that copper powder may be utilized to prepare diphenoquinones from 2,6-dialkyl-4-halophenols. Similarly, various copper salts and combinations or complexes prepared from copper salts and a variety of nitrogencontaining compounds have been disclosed as useful in the preparation of both diphenoquinones and polyphenoxy ethers. These include, for example, cupric salts of primary and secondary amines (U.S. Pat. No. 3,306,874 issued to Hay); and cupric salts of tertiary amines (U.S. Pat. No. 3,306,875 issued to Hay and U.S. Pat. No. 3,134,753 issued to Kwiatek). The use of cupric salts of carboxylic acids as the oxidizing agent in oxidative coupling reactions is also disclosed in the art. See, in this regard, U.S. Pat. No. 3,247,262 issued to Kaeding.

A variety of basic compounds have also been employed in oxidative coupling reactions. In many of these, such as those disclosed in U.S. Pat. No. 2,905,674 issued to Folbey, and in U.S. Pat. No. 2,785,188 issued to Coe, the function of the alkaline material was to react with an acidic component, such as HCl, liberated during the course of the reaction and, therefore, a stoichiometric amount of the base was used.

It should be noted that, all of the previous methods of preparing coupled products from alkyl- or alkoxy- phenols have required the use of either organic solvents or stoichiometric amounts of organic reagents. There has not previously been available a catalyst system useful in the preparation of carboncarbon coupled phenols or naphthols in an aqueous reaction medium. Also, with most of the prior art systems the resulting product or products were determined by the particular catalyst employed and could not easily be controlled. Thus, there has not been available a system which could be modified to produce either the biphenol or diphenoquinone derivative directly from the reaction mixture.

In accordance with the present invention, it has been found that alkyl- or alkoxy- phenols and 1-naphthols may be oxidatively coupled in an aqueous medium if there is employed as a catalyst a mixture of a specific copper compound, and anionic surfactant and an alkaline material. It has also been found that the type of product which is produced can be controlled by the amount of alkaline material employed in the catalyst. By comparison, the prior art catalysts and processes employing said catalysts have a number of disadvantages which have restricted the utility of said catalysts and processes. These include (a) the requirement that the reaction be conducted in an organic solvent, (b) the fact that the primary product produced is often the polyphenoxy ether, and (c) the inability to form the biphenol, bisphenol or binaphthol derivative directly without requiring that this material be produced by a subsequent hydrogenation of the diphenoquinone, stilbenequinone or dinaphthenoquinone prepared in the oxidative coupling reaction. These disadvantages have been overcome by the use of the catalyst and process of the present invention as is described in detail hereinafter.

SUMMARY OF THE INVENTION

In accordance with the present invention, condensation products such as diphenoquinones, stilbenequinones, bisphenols, biphenols, dinaphthenoquinones and binaphthols are selectively prepared by contacting an aqueous mixture of an alkylphenol, an alkoxyphenol or a 1-naphthol with oxygen or an oxygen-containing gas in the presence of a catalyst composition comprising a copper compound, an anionic surfactant and an alkaline material. The phenols or naphthols, copper compounds, surfactants and alkaline materials which may be utilized are critical to the present invention and are described in detail below.

DESCRIPTION OF THE PREFERRED EMBODIMENTS

As mentioned above, in accordance with the present invention condensation products obtained by the carbon-carbon coupling of alkylphenols, alkoxyphenols or 1-naphthols are prepared, in an aqueous medium, by contacting a solution of the phenol or naphthol with oxygen or an oxygen-containing gas in the presence of a copper compound, an anionic surfactant, and an alkaline material. Each of these compounds is described in detail below.

Phenols/Naphthols

The phenols which may be employed in carrying out the present invention include both alkylphenols and alkoxyphenols. The specific phenols which may be utilized are described in detail below.

The first type of alkylphenols which may be utilized are defined as any alkylphenol having at least two alkyl substituents and only one unsubstituted position ortho or para to the hydroxyl group. In other words, the phenols must have at least two alkyl substituents and the substituents must be in the ortho, ortho (2,6 in the formula below) or ortho, para (2,4 in the formula below) positions. These phenols are frequently referred to by the position of the alkyl substituent or substituents on the benzene ring as set forth in the following formula:

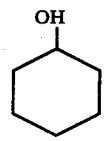

However, in the process of the present invention, when an ortho, para substituted phenol is used, at least one of the alkyl groups in the ortho (2) or para (4) position must be a tertiary alkyl and when an ortho (2), ortho (6) substituted phenol is used only one of the ortho substituents may be a tertiary alkyl. In addition to dialkylphenols, tri- and tetra- substituted materials may also be utilized provided that the substituents in the ortho and para positions satisfy the criteria set forth above.

Thus, these alkylphenols will have one of the following formulas:

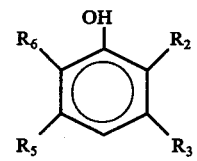

I wherein $R_2$ and $R_6$ are alkyl groups containing from 1 to about 12 carbon atoms, provided that only one of said alkyl groups may be a tertiary alkyl, and $R_3$ and $R_5$ are hydrogen or alkyl groups containing from 1 to about 12 carbon atoms provided that if both $R_3$ and $R_5$ are alkyl only one of said alkyl groups may be a tertiary alkyl.

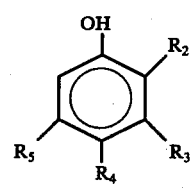

II wherein $R_2$ and $R_4$ are alkyl groups containing from 1 to about 12 carbon atoms, provided that at least one of said alkyl groups is a tertiary alkyl and $R_3$ and $R_5$ are hydrogen or alkyl.

As used herein, the term alkyl refers to any monovalent radical derived from a saturated aliphatic hydrocarbon by removal of one hydrogen atom therefrom. The term includes both straight chain and branched chain materials containing from 1 to about 12 carbon atoms. Preferred results are achieved with alkylphenols wherein the alkyl substituent contains from 1 to about 5 carbon atoms.

The alkyl substituents are referred to herein as primary, secondary or tertiary alkyl depending upon the greatest number of carbon atoms attached to any single carbon atom in the chain. Thus, a primary alkyl has up to 1 carbon atom attached to any single carbon atom as in methyl, ethyl, n-propyl and n-butyl. A secondary alkyl has two carbon atoms attached to a single carbon atom as in isopropyl, isobutyl and secondarybutyl. A tertiary alkyl has three carbon atoms attached to a single carbon atom as in tertiarybutyl.

Condensation products of any alkylphenol coming within the above-mentioned definition may be prepared in accordance with the present invention. As is apparent from that definition, the alkylphenols include dialkylphenols, trialkylphenols, and tetraalkylphenols. Specifically, the phenols which may be utilized include the following:

ortho, para substituted phenols including 2,4-dialkylphenols, 2,3,4-trialkylphenols, 2,4,5-trialkylphenols, and 2,3,4,5-tetraalkylphenols wherein the alkyl groups are either methyl or a primary, secondary, or tertiary alkyl provided that at least one of the alkyl groups in either the 2 or the 4 position is a tertiary alkyl, and ortho, ortho substituted phenols including 2,6-dialkylphenols, 2,3,6-trialkylphenols and 2,3,5,6-tetraalkylphenols wherein the alkyl groups are either methyl or a primary, secondary, or tertiary alkyl provided that at least one of the alkyl groups in either the 2 or the 6 position is either a primary or secondary alkyl.

Representative ortho, para-substituted phenols which may be used include, for example, 2,4-ditertiarybutylphenol, 2-methyl-4-tertiarybutylphenol, 2-tertiarybutyl-4-methylphenol, 2,4-ditertiaryamylphenol, 2,4-ditertiaryhexylphenol, 2-isopropyl-4-tertiarybutylphenol, 2-secondarybutyl-4-tertiarybutylphenol, 2-tertiarybutyl-3-ethyl-4-methylphenyl, 2-octyl-3-dodecyl-4-tertiarybutylphenol, 2,5-dimethyl-4-tertiarybutylphenol, 2-tertiarybutyl-4,5 dioctylphenol and 2-methyl-3-ethyl-4-tertiarybutyl-5-nonylphenol.

Representative 2,6-dialkylphenols (ortho, orthosubstituted) include, for example, 2,6-xylenol, 2-methyl-6-butyl phenol, 2,6-diisobutyl phenol, 2-octyl-6-methyl phenol, 2-isobutyl-6-dodecyl phenol, 2-ethyl-6-methyl phenol, 2,6-dodecyl phenol, 2-methyl-6-tertiary-butyl phenol, 2,6-diisopropyl phenol, and 2-cyclohexyl-6-methyl phenol. In this regard, it should be emphasized that 2,6-dialkylphenols wherein both alkyl substituents are tertiary alkyl groups may not be employed in accordance with the present invention. This is contrary to many of the teachings in the art which indicate that 2,6-ditertiaryalkylphenols such as 2,6-ditertiarybutylphenol are the most easily oxidatively coupled of the phenols.

Representative 2,3,6-trialkylphenols which may be utilized in accordance with the present invention include, for example, 2,3,6-trimethyl phenol, 2,3,6-triethyl phenol, 2,6-dimethyl-3-ethyl phenol, 2,3-diethyl-6-tertiary-butyl phenol, 2,3,6-tridecyl phenol, and 2-octyl-3-decyl-6-dodecyl phenol.

Representative 2,3,5,6-tetraalkylphenols which may be utilized in accordance with the present invention include, for example, 2,3,5,6-tetramethyl phenol, 2,3,5-trimethyl-6tertiarybutyl phenol, 2,3,6-trimethyl-5-tertiary-butyl phenol, 2,3-dimethyl-5,6-diethyl phenol, 2,3,5,6-tetradodecyl phenol, and 2-methyl-3-ethyl-5-isopropyl-6-butylphenol.

When an ortho, para substituted alkylphenol is employed the coupling reaction proceeds in accordance with the following reaction resulting in the o, o' coupled product.

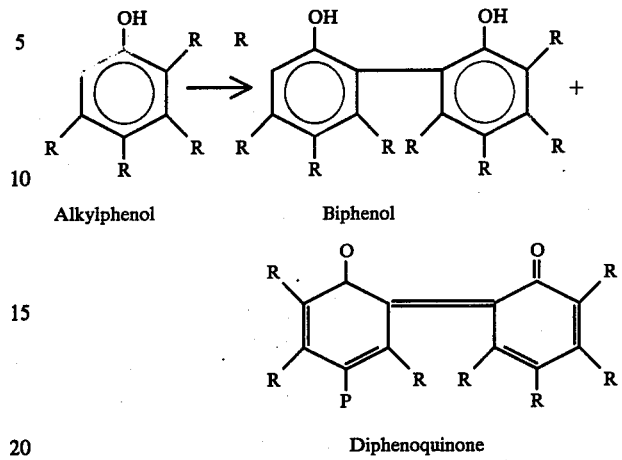

Alkylphenol    Biphenol

Diphenoquinone

In this reaction R represents hydrogen or an alkyl group as defined above depending upon whether a di, tri, or tetra substituted alkylphenol is utilized.

Similarly, with the ortho, ortho-substituted alkylphenols, the reaction results in the p, p'-coupled product in accordance with the following reaction wherein R is hydrogen or alkyl depending upon which of the above-mentioned alkylphenols is used at the starting material.

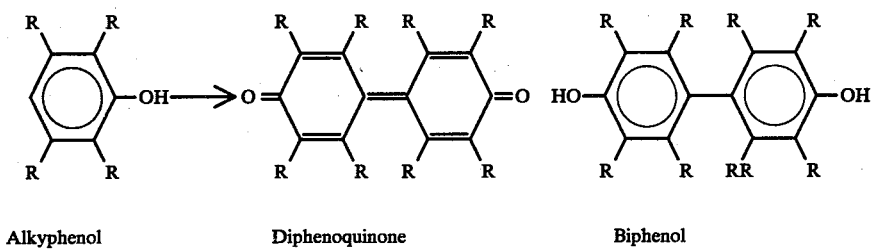

Alkyphenol    Diphenoquinone    Biphenol

It has also been found that certain alkoxyphenols may be oxidatively coupled in accordance with the present invention. These include 2,6-disubstituted phenols wherein at least one of the substituents is an alkoxy group containing up to about six carbon atoms such as methoxy, ethoxy, propoxy, butoxy and pentoxy. In addition to the 2,6-dialkoxyphenols, 2-alkyl-6-alkoxyphenols, wherein the alkyl groups are as defined above for the alkylphenols, may be utilized. As used herein, the term alkoxyphenols is intended to include both types of compounds. These compounds may be represented by the following general formulas:

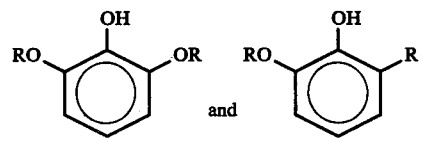

and wherein R is an alkyl group containing from 1 to about 12 carbon atoms and OR is an alkoxy group containing from 1 to about 6 carbon atoms. As above, R may be either methyl or a primary, secondary, or tertiary alkyl and may contain from 1 to about 12 carbon atoms and preferably contains from 1 to about 5 cabon atoms. Representative alkoxyphenols which may be utilized include, for example, 2,6-dimethoxyphenol, 2,6-diethoxyphenol, 2,6-dibutoxyphenol, 2-methoxy, 6-pentoxyphenol, 2-methyl-6-methoxyphenol, 2-decyl-6-butoxyphenol and 2-ethyl-6-propoxyphenol.

When these phenols are utilized the reaction proceeds in accordance with the following representative reaction resulting in the p, p'-coupled material.

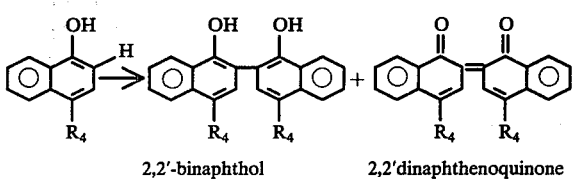

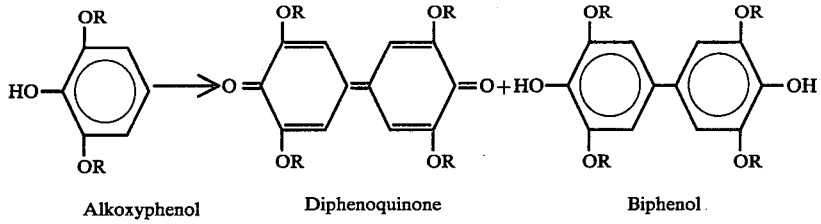

Mixtures of 2 different phenols may also be utilized. When this is done, there generally results a mixture of three different materials. Two of these are the products of the oxidative coupling of one mol of one of the phenols with a second mol of the same phenol. The third product is that resulting from the oxidative coupling of one mol of the first phenol with one mol of the second phenol. The products may be separated prior to use.

Finally, 1-naphthol and substituted 1-naphthols having at least 1 unsubstituted position ortho or para to the hydroxyl group may be employed. The preferred naphthols which may be coupled in accordance with the present invention are represented by the following general formula:

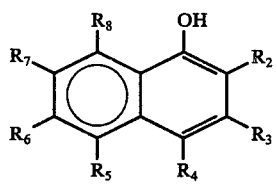

wherein $R_2$, $R_3$ and $R_4$ are hydrogen, alkyl containing from 1 to 5 carbon atoms, or alkoxy containing from 1 to 6 carbon atoms, provided that either $R_2$ or $R_4$ must be hydrogen and, preferably, both $R_2$ and $R_4$ are hydrogen; and $R_5$, $R_6$, $R_7$ and $R_8$ are hydrogen, alkyl containing from 1 to 5 carbon atoms or alkoxy containing from 1 to 6 carbon atoms provided that tertiary alkyl or alkoxy groups may not be attached to adjacent carbon atoms of the naphthalene molecule.

Representative naphthols which may be utilized include, for example, 1-naphthol, 2-methyl-1-naphthol, 2,3-dimethyl-1-naphthol, 4-ethyl-1-naphthol, and 2-methoxy-1-naphthol.

When a naphthol is employed, the coupling reaction takes place in accordance with the following general reactions depending upon the reactive positions — i.e., those either ortho or para to the hydroxy group — available. Thus, if $R_2$ is hydrogen and $R_4$ is alkyl or alkoxy Similarly, if $R_4$ is hydrogen and $R_2$ is alkyl or alkoxy, the products are the 4,4'-binaphthol and the 4,4'-dinaphthenoquinone. When both $R_2$ and $R_4$ are hydrogen the products may be a mixture of the 2,2'; 2,4' and 4,4'-binaphthols and -dinaphthenoquinones.

Copper Compound

One of the essential components of the catalyst composition of the present invention and of the improved method of preparing carbon-carbon coupled products of phenols and naphthols is a copper compound. Not any copper compound may be employed and it is critical that the copper compound be selected from the following list of cupric and cuprous materials:

cupric halides, such as cupric chloride, cupric bromide, cupric fluoride and cupric iodide, basic cupric halo hydroxides represented by the formula $CuX_2 \cdot Cu(OH)_2$ wherein X is chlorine, fluorine, bromine, or iodine, cuprous halides, such as cuprous chloride, cuprous bromide, cuprous fluoride and cuprous iodide, cupric carboxylates, such as cupric acetate cupric benzoate, and cupric butyrate cupric nitrate, cupric sulfate, cupric alkyl sulfates wherein the alkyl group is either a straight or branched chain alkyl containing from 1 to about 20 carbon atoms including, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl, cupric aryl sulfonates wherein the aryl group contains at least one aromatic ring which may, if desired, have alkyl substituents such as those mentioned above, attached thereto including, for example, benzene, naphthalene, anthracene, dodecyl benzene, methyl naphthalene, and hexadecyl anthracene, cupric carbonate, basic cupric carbonate — i.e., $CuCo_3 \cdot Cu(OH)_2$, cupric hydroxide, cupric chlorate — i.e., $Cu(ClO_3)_2$, cuprous red oxide ($Cu_2O$) commonly referred to as cuprite.

If either cupric nitrate or cupric sulfate is employed as the copper compound these materials may be prepared in situ in the reaction medium by adding thereto a material, such as cupric nitrite or cupric sulfite, which is oxidized to the desired nitrate or sulfate in the reaction vessel.

Also, if a cupric alkyl sulfate wherein the alkyl group contains at least 8 carbon atoms is employed, this material may function both as the copper compound and the anionic surfactant and it is, therefore, not necessary to include a separate surfactant in the catalyst system. However, with a cupric alkyl sulfate wherein the alkyl group contains from 1 to 7 carbon atoms a surfactant must be added and even when the alkyl group contains at least 8 carbon atoms, a separate surfactant may be employed.

The amount of copper compound employed has not been found to be narrowly critical to the utility of the catalyst system in carrying out the improved process of the present invention. However, to achieve a significant increase in the amount of carbon-carbon coupled product, there is generally included in the reaction mixture at least about 0.005 millimols of copper compound per mol of phenol or naphthol. Preferred results are achieved when the amount of copper compound employed is equal to about .04 millimols per mol of phenol or naphthol. Additional amounts of the copper compound may be employed. However, the use of greater amounts of the copper compound has not generally been found to significantly increase the total yield of product and it is, therefore, not generally desirable to include additional material in the reaction mixture.

Surfactant

The catalyst composition of the present invention also includes, as an essential component thereof, an anionic surfactant. A variety of surfactants are well known in the art and, as used herein, the term surfactant is intended to refer to organic compounds that contain in the molecule two dissimilar structural groups, such as a water-soluble and a water-insoluble moiety.

Surfactants are often classified, based on the hydrophilic (water linking) group which they contain, as either anionic, cationic, nonionic, or amphoteric. Only those surfactants classified as anionic may be employed in the present invention. As used herein, the term anionic surfactant refers to surfactants in which the hydrophilic moiety is negatively charged in an aqueous solution or dispersion.

Anionic surfactants are discussed in detail in the *Encyclopedia of Chemical Technology*, Kirk-Othmer, Second Edition Vol. 19 at pages 512–531, and any of the surfactants described therein may be utilized in the present invention.

Preferred anionic surfactants are those in which the hydrophilic moiety is either a carboxylate, phosphate, sulfate or sulfonate group. The surfactants are described below simply by reference to these groups — i.e., as carboxylates, etc. Especially preferred results have been achieved with the sulfates and sulfonates.

Representative carboxylates which may be employed include, for example, soaps and aminocarboxylates. The soaps may be represented by the following general formula (R COO)⁻ (M)⁺ wherein

R is an alkyl group generally containing from 9 to 21 carbon atoms, and

M is a metallic or amine ion.

Aminocarboxylate surfactants include, for example, N-acylsarcosinates obtained by the condensation reaction of a fatty acid chloride and sarcosine (N-methyl glycine) and acylated protein hydrolyzates prepared by reacting a protein hydrolyzate with a fatty acid or a fatty acid chloride.

Representative phosphate surfactants which may be employed include, for example, alkyl phosphates such as di(2-ethylhexyl) phosphate; alkyl polyphosphates, such as (2-ethylhexyl)$_5$ Na$_5$(P$_3$O$_{10}$)$_2$; ethoxylated phosphate esters; and partial phosphate esters of nonionic surfactants such as those prepared by reacting an ethoxylated alcohol, an ethoxylated alkylphenol or a polyoxypropylene-polyoxyethylene copolymer with a phosphorylating agent such as P$_2$O$_5$, polyphosphoric acid or POCl$_3$.

Sulfates which may be employed include, for example, alkyl sulfates having the formula ROSO$_3$M wherein R is a linear or branched chain alkyl group such as lauryl, heptadecyl, cetyl, oleyl, 2-ethylhexyl, octyl or tallow and M is a metallic or amine ion such as sodium, potassium, ammonium, magnesium, diethanolamine, or triethanolamine. Cupric alkyl sulfates which can be employed as the surfactant were discussed above in the section entitled Copper Compound.

sulfated natural fats and oils such as those prepared by reacting animal, vegatable or fish oils, for example, tallow, castor oil, sperm oil, coconut oil, cod's oil, neat'sfoot oil, peanut oil, soybean oil or rice-bran oil with a sulfating agent such as sulfuric acid, sulfated oleic acid such as the disodium salt of sulfated oleic acid, sulfated alkanolamides such as the sodium salt of the half sulfate ester of lauric ethanolamide, and materials prepared by reacting a sulfating agent with a mono- or diethanolamide of any fatty acid containing from about 12 to about 18 carbon atoms, sulfated esters such as those repesented by the following formula CH$_3$(CH$_2$)$_7$CH$_2$CH(OSO$_3$Na)CH$_2$(CH$_2$)$_5$—CH$_2$.
COOR wherein R is ethyl, propyl, butyl or amyl, sulfated polyoxyethylene alkylphenols, such as the ammonium and sodium salts of the sulfate esters of nonylphenoxytri(ethyleneoxy)ethanol and dodecylphenoxypenta(ethylenoxy)ethanol, and alkylpolyoxyethylene sulfates such as those represented by the following formula R(O CH$_2$ CH$_2$)$_m$ OSO$_3$M wherein R is a linear or branched chain alkyl group such as lauryl, tridecyl, dodecyl, coco or myristyl, $m$ is an integer equal to at least 1, and M is a metallic or amine ion such as ammonium, sodium, potassium or triethanolamine.

The final group of preferred surfactants are the sulfonates including, for example, alkane sulfonates such as those prepared by reacting a saturated hydrocarbon with SO$_2$ and Cl$_2$ and hydrolyzing the resulting alkylsulfonyl chloride to the sulfonic acid, alkylbenzenesulfonates including both linear and branched materials such as the alkali metal, alkaline earth metal and amine salts of docecylbenzenesulfonic acid and tridecylbenzenesulfonic acid as well as the free acids, petroleum sulfonates such as the water-soluble green soaps and the oil-soluble mahogany soaps, dialkyl sulfosuccinates such as sodium dioctylsulfosuccinate, sodium di(2-ethylhexyl)sulfosuccinate, and sodium diamyl sulfosuccinate, naphthalenesulfonates such as salts of alkylnaphthalenesulfonates, salt of naphthalenesulfonates, salts of tetrahydronaphthalenesulfonates and salts of sulfonated formaldehyde-naphthalene condensates, N-acyl-N-alkyltaurates such as sodium-N-oleoyl-N-methyltaurate, sodium-N-palmitoyl-N-methyltaurate, and sodium-N-tall oil-N-methyltaurate, Beta sulfoesters — i.e., 2-sulfoethyl esters of fatty acids having the formula R COO $CH_2CH_2SO_3Na$, wherein RCOO is derived from a fatty acid, and olefin sulfonates such as those prepared by sulfonating an alpha olefin containing from 15 to 18 carbon atoms.

The amount of surfactant employed has not been found to be narrowly critical to the utility of the catalyst system in carrying out the improved process of the present invention. However, to achieve a significant increase in the amount of carbon-carbon coupled product, there should be included in the reaction mixture at least about 0.04 mmols of surfactant per mol of phenol or naphthol. Preferred results are achieved when the amount of surfactant employed is equal to from about 0.8 to about 1.6 mmols of surfactant per mol of phenol or naphthol. Additional amounts of the surfactant may be employed; however, the use of greater amounts of surfactant has usually not been found to significantly increase the total yield of product and it is, therefore, not generally desirable to include additional material in the reaction mixture. When a cupric alkyl sulfate as defined above is employed, both as the copper compound and as the surfactant, the amount of said material employed is preferably equal to at least 0.45 mmols per mol of phenol or naphthol — i.e., the preferred amount of copper compound plus the preferred amount of surfactant.

Alkaline Material

In accordance with the present invention, an alkaline material is also included in the catalyst composition. It has been found that the use of an alkaline material in the present system increases the conversion to carbon-carbon coupled products and decreases the conversion to carbon-oxygen coupled products. The use of such a material also increases the rate of the oxidative coupling reaction and decreases the amount of the copper compound which must be utilized.

The alkaline material useful is achieving the improved results of the present invention is selected from the group consisting of alkali metal hydroxides, alkali metal carbonates, and alkali metal bicarbonates. The alkaline material may be added either as a single compound or as a mixture of compounds. Representative materials which may be employed include, for example, sodium hydroxide, potassium hydroxide, lithium hydroxide, sodium carbonate, lithium carbonate, sodium bicarbonate, rubidium carbonate, rubidium hydroxide, cesium bicarbonate, and cesium hydroxide.

The amount of alkaline material employed has not been found to be narrowly critical to the present invention. However, preferred results are achieved when the amount of said material is equal to at least about 3 millimols per mol of phenol or naphthol. Increased amounts of alkaline material may also be utilized in carrying out the present invention. It has been found that, for a given set of reaction conditions, increasing the amount of alkaline material increases the total conversion to carbon-carbon coupled products and the relative amount of diphenoquinone stilbene quinone or dinaphthenoquinone as compared to the amount of biphenol, bisphenol or binaphthol. Thus, by varying the amount of alkaline material the type of product can be controlled.

Besides the selective production of carbon-carbon coupled products, an additional advantage of the catalyst system of the present invention is the ability to control the type of carbon/carbon coupled product produced. Thus, it is possible to prepare selectively either diphenoquinone or biphenol, stilbene quinone or bisphenol, or dinaphthenoquinone or binaphthol in accordance with the present invention. This result is achieved by controlling the amount of alkaline material included in the system. Generally, as the amount of alkaline material is increased, the percentage of quinone derivative produced also increases.

As mentioned above, an advantage of the catalyst system and process of the present invention is that it makes it possible for the oxidative coupling reaction to be carried out in an aqueous medium. The amount of water employed has not been found to be critical to the present invention and any amount of water which will permit the reaction mixture to be stirred during the course of the reaction may be employed. It should also be noted again that it is not essential that the various components be soluble in water and the term aqueous mixture as used herein is intended to include solutions, slurries, suspensions and the like.

The components of the reaction mixture may be combined in any suitable manner. Thus, the phenol or naphthol, surfactant, copper compound, alkaline material and water may be combined in any order in a suitable reaction vessel. Alternatively, and in a preferred method, the phenol or naphthol and surfactant are combined in water in a suitable reaction vessel, the mixture is heated to from 50° to 60° C. and an aqueous mixture of the copper compound is added thereto followed by an aqueous solution of the alkaline material. In modifications of this procedure the copper compound may be added prior to heating or the copper compound and alkaline material may be combined prior to addition to the reaction mixture.

The reaction mixture comprising phenol or naphthol, water, surfactant, copper compound, and alkaline material is contacted with a suitable oxidizing agent to convert the phenol or naphthol to the desired product. Oxidizing agents which may be employed in carrying out the present invention include oxygen either alone or as an oxygen-containing gas, such as air. The oxygen may be introduced into the reaction mixture either directly as oxygen gas or as an oxygen-generating material such as ozone, hydrogen peroxide, or an organic peroxide. The amount of oxygen utilized should be sufficient to obtain the desired conversion of the phenol or naphthol to the coupled product. To assure that sufficient oxygen is present, oxygen should be introduced into the reaction mixture continuously during the course of the reaction.

The reaction conditions — i.e., time and temperature — employed have not been found to be narrowly critical to the process of the present invention. Preferred results have been achieved when the reaction mixture is maintained at from about 80° to 90° C. during the course of the reaction. However, temperatures above and below this preferred range may be utilized. At lower temperatures the reaction rate is reduced and at temperatures below about 40° C. is so slow as to result in an uneconomic system. Similarly, when operating at atmospheric pressure, as is desirable in some commercial operations, the practical upper limit on the temperature is 100° C., the boiling point of the water.

If the reaction is conducted at increased oxygen pressure, the reaction time is decreased, the total yield of coupled product is increased, and the relative amount of quinone derivative is increased.

The amount of time required for completion of the reaction depends on the temperature employed and the other variables such as the pressure, concentration or naphthol and the amount of copper compound, surfactant, and alkaline material employed. However, it has been found that, when conducted at atmospheric pressure, the reaction is completed in 6 hours or less.

Although, as mentioned above, the process of the present invention results primarily in the production of carbon-carbon coupled products, there are also sometimes included in the solids removed from the reaction mixture the following: (a) unreacted phenol or naphthol, and (b) low molecular weight polyphenoxy ether. The polyphenoxy ether and phenol or naphthol may be removed by washing the solids with a solvent in which these materials are soluble, such as an aromatic hydrocarbon — e.g., benzene, or a halogenated solvent — e.g., methylene chloride. It it is desired to separate the materials from each other and from the solvent, this may be done by distillation.

If the reaction results in the mixture of biphenol and diphenoquinone, bisphenol and stilbene quinone, or binaphthol and dinaphthenoquinone, these materials may be separated by any method known in the art. An especially convenient way of separating the materials is to stir the solid product with a dilute aqueous solution of sodium hydroxide, which has the effect of converting the biphenol, bisphenol or binaphthol to the sodium salt which is soluble in water. The insoluble diphenoquinone, stilbene quinone or dinaphthenoquinone may then be filtered off and the biphenol, bisphenol or binaphthol recovered by adding the aqueous solution of the sodium salt thereof to a dilute solution of a strong acid such as hydrochloric acid from which the biphenol, bisphenol or binaphthol precipitates. Alternatively, the entire product may be hydrogenated or chemically reduced and converted to only the biphenol, bisphenol or binaphthol.

The diphenoquinones and/or biphenols as well as the binaphthols, bisphenols and dinaphthenoquinones and stilbene quinones produced in accordance with the present invention are suitable for any of the uses of these materials which have heretofore been described in the art. Thus, the diphenoquinones and dinaphthenoquinones may be used as inhibitors of oxidation, peroxidation, polymerization and gum formation in gasolines, aldehydes, fatty oils, lubricating oils, ethers and similar compounds as mentioned in U.S. Pat. No. 2,905,674 issued to Filbey. The diphenoquinones may also be hydrogenated, employing conventional techniques, to yield the corresponding biphenol. The biphenols may be employed as stabilizers in gasoline and other petroleum products as described in U.S. Pat. No. 2,479,948 issued to Luten et al.

The catalyst system of this invention may also be employed to prepare coupled products of alkylphenols wherein all of the positions ortho and para to the hydroxy group ae substituted and the substituent para to the hydroxy group is methyl. These alkylphenols may be represented by the following general formula:

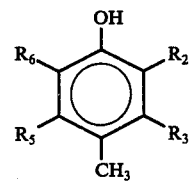

wherein $R_3$ and $R_5$ are hydrogen, alkyl groups containing from 1 to about 5 carbon atoms or alkoxy groups containing from 1 to about 6 carbon atoms, provided that if both $R_3$ and $R_5$ are alkyl or alkoxy groups only one or these groups may be a tertiary alkyl or alkoxy; and $R_2$ and $R_6$ are a primary, secondary or tertiary alkyl containing from 1 to about 12 carbon atoms or an alkoxy group containing from 1 to about 6 carbon atoms provided that only one of said substituents may be a tertiary alkyl or alkoxy.

Representative compounds which may be employed include, for example, 2,4,6-trimethyl phenol; 2,6-disecondary butyl-4-methyl phenol; 2-methyl-6-t-butyl-4-methyl phenol; and 2,3,4,6-tetramethyl phenol.

When one of these alkylphenols is employed the reaction proceeds in accordance with the following general reaction to produce the stilbene quinone or bisphenol derivative. These materials are useful in the same applications set forth above for the diphenoquinones, dinaphthenoquinones, biphenols and binaphthols.

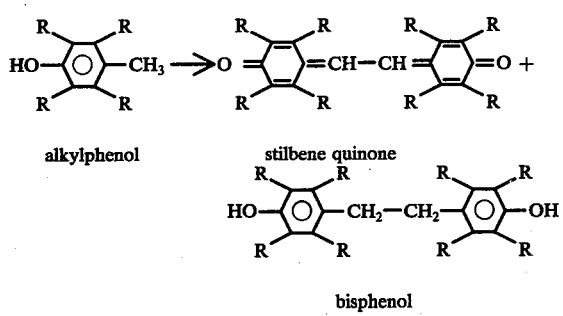

alkylphenol     stilbene quinone bisphenol

In carrying out this reaction, the same procedures and conditions are employed as those given above for the other alkylphenols, alkoxyphenols and naphthols. However, with these particular phenols it has been found that the preferred amount of alkaline material employed is equal to at least about 1 mol per mol of phenol. When less than this amount is utilized the total conversion as well as the yield of carbon-carbon coupled product are reduced.

In order to describe the present invention so that it may be more clearly understood, the following examples are set forth. These examples are set forth primarily for the purpose of illustration and any enumeration of detail contained therein should not be interpreted as a limitation on the concept of the present invention.

As used herein, the term percent refers to:

$$\frac{\text{mols of product (actual)}}{\text{mols of product (theoretical)}} \times 100$$

EXAMPLE 1

Into a 500 ml., creased Morton flask, fitted with a gas addition tube, a condenser, a thermometer and a stirrer capable of operating at speeds in the range of from about 8,000 to about 10,000 rpm., there were added
- 48.8 grams (400 mmoles) of 2,6-xylenol,
- 0.20 gram (0.6 mmoles) of sodium lauryl sulfate, and
- 150 ml of ion exchanged water.

The mixture was stirred under oxygen and heated to a temperature of 55° C. At that time a solution of 0.4 gram (2 mmoles) of cupric acetate monohydrate in 50 ml of water was added. There was then added dropwise, over a period of 1½ minutes, 8 ml of a 1.0 N-sodium bicarbonate solution.

The reaction mixture was heated to a temperature of 80° C. and a slow stream of oxygen was introduced. At the end of 6 hours, the reaction was flushed with nitrogen and cooled to a temperature if 20° C.

The reaction mixture was filtered through a medium porosity, sintered-glass funnel under slight vacuum. The recovered solid was washed with water and filtered again. A sample of the solid was removed and any unreacted 2,6-xylenol was determined by GLC analysis. The analysis indicated 8 mol percent of unreacted 2,6-xylenol.

The water-washed solid was air dried and washed twice with 150 ml of benzene to remove 2,6-xylenol and polyphenoxy ether. The resulting yellow solid was dried at 60° C. The yield of tetramethyl biphenol was equal to 80 mol percent.

EXAMPLES 2 – 18

Into the reaction flask described in Example 1, there were added, also as described in Example 1,
- 48.8 grams (400 mmols) of 2,6-xylenol,
- 0.4 gram (2 mmols) of cupric acetate,
- 200 ml of ion exhanged water,
- 8 ml of a 1.0 N-solution of sodium bicarbonate, and
- a surfactant as indicated in Table I.

The reaction mixture was heated to a temperature of 80° C. for 6 hours during which time oxygen was introduced as in Example 1. At the end of this time, the product was recovered, analyzed for residual 2,6-xylenol, and the products filtered and washed as in Example 1. If the benzene washed solid was green in color (in Examples 5, 6, 7, 11, 15 and 16), this indicated the presence of diphenoquinone. This material was separated from the biphenol by moistening the solids with methanol, stirring the moistened solids in water and added to the resulting suspension solid sodium hydroxide pellets, in an amount equal to the total weight of the solids, to dissolve the biphenol. The resulting suspension was filtered and the filtrate containing the biphenol was added to a dilute solution of hydrochloric acid in an amount sufficient to neutralize the sodium hydroxide and precipitate the bisphenol. The biphenol was then filtered off, dissolved in acetone and precipitated with water to yield a crystalline biphenol which was filtered, washed with water and dried at 60° C. The solid diphenoquinone from the sodium hydroxide solution was washed with water until the filtrate had a neutral pH and was dried at 60° C.

TABLE I

| Example | Surfactant Code* | Amount grams | Amount mmols | Diphenoquinone (mol %) | Biphenol (mol %) | Polyphenoxy Ether (mol %) |
|---|---|---|---|---|---|---|
| Control | — | — | | 0 | 28.4 | 51.1 |
| 2 | A | .02 | | 0 | 45.5 | 44.0 |
| 3 | A | .05 | | 0 | 49.7 | 16.9 |
| 4 | A | .10 | | 0 | 50.0 | 4.0 |
| 5 | A | .40 | | 13.1 | 64.5 | 16.4 |
| 6 | A | .55 | | 2.5 | 68.3 | 17.2 |
| 7 | A | 1.10 | | 7.5 | 70.0 | 19.5 |
| 8 | B | 0.20 | | 0 | 59.4 | 36 |
| 9 | C | 0.20 | | 0 | 45.3 | 13.7 |
| 10 | C | 0.10 | | 0 | 62.5 | 5.5 |
| 11 | D | 0.20 | | 9.4 | 73.5 | 11.1 |
| 12 | D | 0.10 | | 0 | 76.5 | 16.5 |
| 13 | E | 0.20 | | 0 | 72.5 | 21.0 |
| 14 | F | 0.20 | | 0 | 53.0 | 22.0 |
| 15 | G | 0.20 | | 6.7 | 66.0 | 25.3 |
| 16 | H | 0.20 | | 19.7 | 59.7 | 18.6 |
| 17 | I | 0.20 | | 0 | 50.0 | 19 |
| 18 | J | 0.20 | | 0 | 49.0 | 15.5 |

*Surfactants
A - sodium lauryl sulfate
B - octa(ethyleneoxy) nonylphenol phosphate
C - potassium hexyl phosphate
D - sodium dodecylbenzenesulfonate
E - sodium butadiene-urea sulfate
F - sodium lauryl phosphate
G - sodium dioctylsulfosuccinate
H - sodium heptadecylsulfate
I - sodium laurate
J - sodium salts of mixed tallow fatty acids available as Cirrasol 23 from ICI United States Inc., Wilmington, Delaware

EXAMPLES 19 – 32

Employing the reaction flask and procedure described in Example 1, there were combined
- 48.8 grams (400 millimols) of 2,6-xylenol,
- 0.2 gram (0.6 millimols) of sodium lauryl sulfate, and
- 150 ml of ion exhanged water.

To the resulting mixture maintained at 55° C. and under an oxygen atmosphere there was added a copper compound of the type and amount indicated in Table II in 50 ml of water, followed by a 1.0 N-solution of sodium bicarbonate also in the amounts indicated in Table II.

The resulting reaction mixture was heated to 80° C. and oxygen was introduced for 6 hours at the end of which time the products were isolated as described in Examples 1 and 2. The yields of the products are also given in Table II.

EXAMPLES 33 – 40

Employing the reaction flask and procedure described in Example 1, there were combined
    48.8 grams (400 millimols) of 2,6-xylenol, The resulting reaction mixture was heated to 90° C. and oxygen was introduced for 6 hours at the end of which time the products were separated as described in Examples 1 and 2. The yields of the products obtained are also given in Table IV.

TABLE II

| | Copper Compound | | | Products | | |
|---|---|---|---|---|---|---|
| | | Amount | 1.0 N NaHCO$_3$ | Diphenoquinone | Biphenol | Polyphenoxy Ether |
| Example | | (grams) | (mmols) | (ml) | (mol %) | (mol %) | (mol %) |
| Control | — | — | — | 8.0 | 0 | 28.6 | — |
| 19 | Cupric Acetate | 0.40 | 2.0 | 8.0 | 0 | 80.0 | 11.0 |
| 20 | Cupric Benzoate | — | 2.0 | 8.0 | 25 | 48.6 | 25.4 |
| 21 | Cupric Nitrate | — | 2.0 | 8.0 | 2 | 75.5 | 14.0 |
| 22 | Cupric Sulfate | — | 2.0 | 8.0 | 8.3 | 72.5 | 15.0 |
| 23 | Cupric Chloride | — | 2.0 | 8.0 | 34.2 | 46.6 | 17.0 |
| 24 | Cupric Carbonate | — | 2.0 | 4.0 | 0 | 65.6 | 13.0 |
| 25 | Cuprous Chloride | — | 2.0 | 6.0 | 9.6 | 70.5 | 14.0 |
| 26 | Cuprous Oxide Red | — | 2.0 | 4.0 | 9.6 | 66.0 | 22.0 |
| 27 | Cupric Acetate | 0.02 | 0.1 | 4.2 | 0 | 75.5 | 17.5 |
| 28 | Cupric Acetate | 0.05 | 0.25 | 4.5 | 0 | 72.5 | 19.5 |
| 29 | Cupric Acetate | 0.10 | 0.5 | 5 | 0 | 66.3 | 16.7 |
| 30 | Cupric Acetate | 0.20 | 1.0 | 6 | 0 | 66.8 | 16.2 |
| 31 | Cupric Acetate | 0.60 | 3.0 | 10 | 0 | 74.3 | 17.7 |
| 32 | Cupric Acetate | 0.80 | 4.0 | 12 | 0 | 78.3 | 18.7 |

TABLE III

| | Cubric Acetate | | Alkaline Material | | Products | | |
|---|---|---|---|---|---|---|---|
| Example | grams | mmols | (1 Normal Soln.) | ml | Diphenoquinone (mol %) | Biphenol (mol %) | Polyphenoxy Ether (mol %) |
| Control | 0.40 | 2.0 | | | 0 | 34.2 | 27.8 |
| 33 | 0.40 | 2.0 | Sodium Bicarbonate | 6 | 0 | 58.8 | 18.2 |
| 34 | 0.40 | 2.0 | Sodium Hydroxide | 6 | 0 | 59.3 | 22.7 |
| 35 | 0.40 | 2.0 | Potassium Carbonate | 6 | 0 | 53.5 | 24.7 |
| 36 | 0.02 | 0.1 | Sodium Bicarbonate | 12.2 | 38.4 | 29.6 | 32.0 |
| 37 | 0.02 | 0.1 | Sodium Bicarbonate | 4.2 | 0 | 75.5 | 17.5 |
| 38 | 0.40 | 2.0 | Sodium Bicarbonate | 8 | 0 | 80 | 11.5 |
| 39 | 0.40 | 2.0 | Sodium Bicarbonate | 10 | 8.8 | 69 | 18.7 |
| 40 | 0.40 | 2.0 | Sodium Bicarbonate | 16 | 0 | 74.5 | 14.5 |

TABLE IV

| | | | Products | | |
|---|---|---|---|---|---|
| Example | Phenol | Amount (gms) | Diphenoquinone (mol %) | Biphenol (mol %) | Polyphenoxy Ether (mol %) |
| 41 | 2,3,6-trimethyl phenol | 56.5 | 0 | 69 | 27 |
| 42 | 2-methyl-6-t-butylphenol | 65.7 | >15 | 0 | <47 |
| 43 | 2,6-di-sec-butylphenol | 82.5 | >90 | 0 | — |

0.2 gram (0.6 millimols) of sodium lauryl sulfate, and
    150 ml of ion exchanged water.

To the resulting reaction mixture at 55° C. there was added a mixture of 50 ml of ion exchanged water and an amount of cupric acetate as indicated in Table III. There was then added a 1.0 N aqueous solution of an alkaline material. The alkaline material employed and the amount of the solution added are also given in Table III.

The resulting reaction mixture was heated to 80° C. and oxygen was introduced for 6 hours at the end of which time the products were isolated as described in Examples 1 and 2. The yields of the products obtained are given in Table III.

EXAMPLES 41 – 43

Employing the reaction flask and procedure described in Example 1, there were combined
    400 millimols of a phenol as identified in Table IV,
    0.20 gram (0.6 millimols) of sodium lauryl sulfate, and
    150 ml of ion exchanged water.

To the resulting mixture at 55° C. there was added a solution of
    0.01 gram (.05 millimol) of cupric acetate, and
    50 ml of ion exchanged water, followed by 16 ml of a 1.0 N-solution of sodium bicarbonate.

EXAMPLE 44

Into the reaction flask described in Example 1, there were added
    48.8 grams (400 mmols) of 2,6-xylenol,
    0.2 gram (0.6 mmols) of sodium lauryl sulfate,
    0.002 gram (0.01 mmol) of cupric acetate monohydrate,
    200 ml of ion exchange water, and
    8 ml of a 1.0 Normal aqueous solution of sodium bicarbonate.

The reaction mixture was stirred, heated to 80° C. and oxygen introduced for 6 hours. At the end of this time, the reactor was flushed with nitrogen and cooled to a temperature of 20° C. The solids were filtered from the reaction mixture and analyzed as described in Examples 1 and 2. Analysis of the product indicated the following:
    polyphenoxy ether — 18.5 mol percent
    diphenoquinone — 0 mol percent
    biphenol — 76.5 mol percent

EXAMPLE 45

Into the reaction flask described in Example 1, there were added
    48.8 grams (400 mmols) of 2,6-xylenol, 0.2 gram (0.6 mmols) of sodium lauryl sulfate,
0.005 gram (0.025 mmol) of cupric acetate monohydrate, and
200 ml of ion exchanged water.

The resulting reaction mixture was stirred under an oxygen atmosphere, heated to 55° C. and there was added thereto 8 ml of a 1.0 Normal solution of sodium bicarbonate. The reaction mixture was then heated to 80° C. and maintained at that temperature for 6 hours during which time oxygen was continuously introduced into the reaction mixture. At the end of six hours, the reaction mixture was flushed with nitrogen and cooled to 20° C. The solids were filtered from the reaction mixture and analyzed as described in Examples 1 and 2.

Analysis of the product indicated 79.5 mol percent of the biphenol, no diphenoquinone, and 15.5 mol percent polyphenoxy ether.

EXAMPLE 46

Into the reaction flask described in Example 1, there were added
48.8 grams (400 mmols) of 2,6-xylenol,
1.2 grams (2 mmols) of cupric lauryl sulfate,
200 ml of ion exchanged water, and
8 ml of a 1.0 Normal solution of sodium bicarbonate.

The reaction mixture was heated to a temperature of 80° C. and maintained at that temperature for 6 hours during which time oxygen was introduced as in Example 1. At the end of this time, the reaction mixture was cooled and the products filtered, washed, and separated as described in Examples 2–18. Analysis of a sample of the recovered product indicated that 95 mol percent of the 2,6-xylenol had reacted. Analysis of the product indicated
16.9 mol percent of polyphenoxy ether,
4.6 mol percent of diphenoquinone, and
73.5 mol percent of biphenol.

EXAMPLE 47

Into a 500 ml creased Morton flask, fitted with a gas addition tube, a condenser, a thermometer and a stirrer capable of operating at speeds in the range of from about 8,000 to about 10,000 rpm, there were added:
82.3 grams (400 mmols) of 2,4-ditertiarybutylphenol
0.20 gram (0.6 mmol) of sodium lauryl sulfate,
0.001 gram (0.05 mmol) of cupric acetate monohydrate, and
150 ml of ion exchanged water.

The resulting reaction mixture was stirred for 5 minutes and there was then added 14.0 ml of a 1.0 Normal solution of sodium bicarbonate. The reaction mixture was stirred 15 minutes, heated to 80° C., and maintained at that temperature for 6½ hrs. during which time oxygen was continuously introduced into the reaction mixture. At the end of this time, the reaction was flushed with nitrogen and cooled to a temperature of 20° C. The reaction mixture was filtered and the solids were washed with 200 ml of water, blended with 200 ml of water, filtered and washed again with 150 ml of water containing 5 ml of concentrated hydrochloric acid. The solids were then washed until the filtrate had a neutral pH. The resulting orange, yellow solids were dried at 60° C. and purified as follows.

57.8 grams of the light orange solids were stirred with 100 ml of ethanol and filtered. The solids were dried at 60° C. resulting in 44 grams of a light cream colored product identified as the 2,2',4,4'-tetratertiarybutyl-6,6'biphenol. The filtrate was evaporated to 20 ml and again filtered after which the solids were washed with methanol resulting in an additional 1.5 grams of the bisphenol.

EXAMPLE 48

Into a 500 ml creased Morton flask, fitted with a gas addition tube, a condenser, a thermometer and a stirrer capable of operating at speeds in the range of from about 8,000 to about 10,000 rpm, there were added:
31.2 grams (200 mmols) of 2,6-dimethoxyphenol,
0.20 gram (0.6 mmol) of sodium lauryl sulfate, and
180 ml of ion exchanged water.

The resulting reaction mixture was stirred and there was then added 0.001 gram (0.05 mmol) of cupric acetate monohydrate, and the reaction mixture was stirred for 15 min. At the end of this time there was added 8.0 ml of a 1.0 Normal solution of sodium bicarbonate. The reaction mixture was stirred 15 min., heated to 80° C., and maintained at that temperature for 6 hrs. during which time oxygen was continuously introduced into the reaction mixture. At the end of this time, the reaction mixture was cooled to a temperature of 25° C. and filtered. The filtrate was acidified with HCl and extracted three times with methylene chloride. The orange material filtered from the reaction mixture was then dissolved in the methylene chloride extract and a sample analyzed indicated no unreacted 2,6-dimethoxyphenol. The methylene chloride was evaporated and the resulting dark red material was washed twice with 100 ml of xylene resulting in 12.2 grams of a reddish-tan solid having a melting point of from 190°–192° C. This material was identified as the tetramethoxybiphenol.

EXAMPLE 49

Into the reaction flask described in Example 48, there was added
31.2 grams (200 mmols) of 2,6-dimethoxyphenol,
0.20 gram (0.6 mmol) of sodium lauryl sulfate, and
180 ml of ion exchanged water.

The resulting reaction mixture was stirred and there was added 0.001 gram (0.05 mmol) of cupric acetate monohydrate. After stirring for an additional 15 min., there was added 14.0 ml of a 1.0 Normal solution of sodium bicarbonate. The reaction mixture was heated to 80° C. and maintained at that temperature for 2 hrs., during which time oxygen was continuously introduced into the reaction mixture. At the end of this time an additional 16.0 ml of a 1.0 Normal solution of sodium bicarbonate was added. The reaction mixture was maintained at 80° C. for an additional 4 hrs. during which time oxygen was continuously introduced. At the end of this time, the reaction mixture was cooled to 25° C. and filtered. The resulting red solid was washed with water and air dried. The dried solid was then washed with 200 ml of xylene and the insoluble solid was dried at 60° C. resulting in 21 grams of a red powder having a melting point of from 190°–192° C. The product was identified as the tetramethoxybiphenol.

EXAMPLE 50

Into a reaction flask described in Example 48, there were added
43.3 grams (300 mmols) of 1-naphthol,
0.20 gram (0.6 mmol) of sodium lauryl sulfate, and
150 ml of ion exchanged water.

The resulting reaction mixture was stirred and there was added 1.0 ml of a solution of 1 gram of cupric acetate monohydrate in 100 ml of ion exchanged water.

After stirring for an additional 15 min., there was added 16.0 ml of a 1.0 Normal solution of sodium bicarbonate. The reaction mixture was heated to 80° C. and maintained at that temperature for 6 hrs., during which time oxygen was continuously introduced into the reaction mixture. At the end of this time, the reaction mixture was cooled to 25° C. and acidified with concentrated HCl to a pH of 1.3. The dark brown precipitate which formed was filtered off, washed with 200 ml of water and air dried resulting in 41.9 grams of a brown solid. Analysis of a sample of the product by gas-liquid chromatography indicated that 84.8 percent of the 1-naphthol had reacted.

The dried solid was then washed with xylene and the insoluble solid was dried at 60° C. resulting in 24.3 grams of a brown solid or a yield of 56 mol percent. Infrared analysis of the product indicated a mixture of the binaphthol and the dinaphthenoquinone.

What is claimed is:

1. A method of preparing a carbon-carbon coupled condensation product of an alkylphenol, an alkoxyphenol or a 1-naphthol, having one of the following formulas

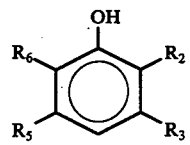

wherein
- $R_2$ and $R_6$ are alkyl groups containing from 1 to about 12 carbon atoms, provided that only one of said alkyl groups may be a tertiary alkyl, and
- $R_3$ and $R_5$ are hydrogen or alkyl groups containing from 1 to about 12 carbon atoms provided that if both $R_3$ and $R_5$ are alkyl only one of said alkyl groups may be a tertiary alkyl;

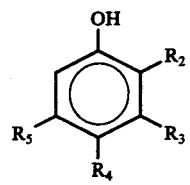

wherein
- $R_2$ and $R_4$ are alkyl groups containing from 1 to about 12 carbon atoms, provided that at least one of said alkyl groups is a tertiary alkyl, and
- $R_3$ and $R_5$ are hydrogen or alkyl;

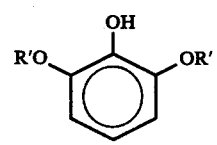

wherein OR' is an alkoxy group containing from 1 to about 6 carbon atoms;

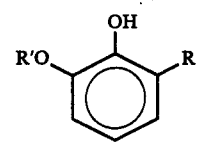

wherein R is an alkyl group containing from 1 to about 12 carbon atoms and OR' is an alkoxy group containing from 1 to about 6 carbon atoms;

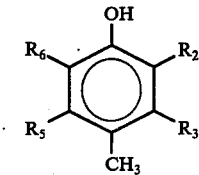

wherein
- $R_3$ and $R_5$ are hydrogen, alkyl groups containing from 1 to about 5 carbon atoms, or alkoxy groups containing from 1 to about 6 carbon atoms provided that if both $R_3$ and $R_5$ are alkyl or alkoxy groups only one of said groups may be a tertiary alkyl or alkoxy; and
- $R_2$ and $R_6$ are alkyl groups containing from 1 to about 12 carbon atoms or alkoxy groups containing from 1 to about 6 carbon atoms provided that only one of said substituents may be a tertiary alkyl or alkoxy; and

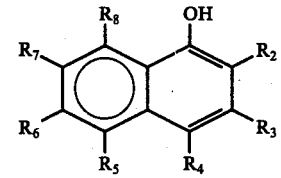

wherein $R_2$, $R_3$ and $R_4$ are hydrogen, alkyl containing from 1 to 5 carbon atoms, or alkoxy containing from 1 to 6 carbon atoms, provided that either $R_2$ or $R_4$ is hydrogen and $R_5$, $R_6$, $R_7$ and $R_8$ are hydrogen, alkyl containing from 1 to 5 carbon atoms or alkoxy containing from 1 to 6 carbon atoms provided that tertiary alkyl or alkoxy groups are not attached to adjacent carbon atoms of the naphthalene molecule, said method comprising contacting an aqueous mixture of the phenol or naphthol with oxygen in the presence of a catalyst consisting essentially of:

a. a copper compound selected from the group consisting of cupric halides, basic cupric halohydroxides, cupric carboxylates, cupric nitrate, cupric sulfate, cupric alkylsulfates, cupric aryl sulfonates, cupric carbonate, basic cupric carbonate, cupric hydroxide, cupric chlorate, cuprous halides, and cuprous red oxide, b. an anionic surfactant in which the hydrophilic moiety is selected from the group consisting of carboxylate, phosphate, sulfate and sulfonate, and c. an alkaline material selected from the group consisting of alkali metal hydroxides, alkali metal carbonates and alkali metal bicarbonates.

2. A method, as claimed in claim 1, wherein the phenol is selected from the group consisting of alkylphenols having at least two alkyl substituents and only one unsubstituted position ortho or para to the hydroxyl group; 2,6-dialkoxyphenols and 2-alkyl-6-alkoxyphenols.

3. A method, as claimed in claim 2, wherein the phenol is an alkylphenol.

4. A method, as claimed in claim 3, wherein the alkylphenol is a 2,6-dialkylphenol.

5. A method, as claimed in claim 4, wherein the alkylphenol is 2,6-xylenol.

6. A method, as claimed in claim 3, wherein the alkyl groups of said alkylphenol contain from 1 to about 5 carbon atoms.

7. A method, as claimed in claim 1, wherein the copper compound is a cupric carboxylate.

8. A method, as claimed in claim 7, wherein the cupric carboxylate is cupric acetate.

9. A method, as claimed in claim 1, wherein the amount of copper compound is equal to at least about 0.005 mmols per mol of phenol or naphthol.

10. A method, as claimed in claim 1, wherein the amount of surfactant is equal to at least 0.04 mmols per mol of phenol or naphthol.

11. A method, as claimed in claim 1, wherein the alkaline material is an alkali metal bicarbonate.

12. A method, as claimed in claim 11, wherein the alkali metal bicarbonate is sodium bicarbonate.

13. A method, as claimed in claim 1, wherein the amount of alkaline material is equal to at least about 3 mmols per mol of phenol or naphthol.

14. A method, as claimed in claim 1, wherein the copper compound and anionic surfactant are a single compound.

15. A method, as claimed in claim 14, wherein the single compound is cupric alkylsulfate wherein the alkyl group contains at least 8 carbon atoms.

16. A method, as claimed in claim 15, wherein the cupric alkylsulfate is cupric lauryl sulfate.

17. A method, as claimed in claim 1, wherein the phenol is an alkylphenol having the following formula:

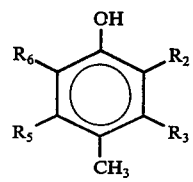

wherein
$R_3$ and $R_5$ are hydrogen, alkyl groups containing from 1 to about 5 carbon atoms, or alkoxy groups containing from 1 to about 6 carbon atoms, provided that if both $R_3$ and $R_5$ are alkyl or alkoxy groups only one of said groups may be a tertiary alkyl or alkoxy, and
$R_2$ and $R_6$ are alkyl groups containing from 1 to about 12 carbon atoms or alkoxy groups containing from 1 to about 6 carbon atoms provided that only one of said substituents may be a tertiary alkyl or alkoxy.

18. A method, as claimed in claim 17, wherein the alkyl phenol is 2,4,6-trimethylphenol.

19. A method, as claimed in claim 17, wherein the amount of alkaline material is equal to at least about 1 mol per mol of alkylphenol.

20. A method, as claimed in claim 1, wherein a naphthol having the following formula is employed:

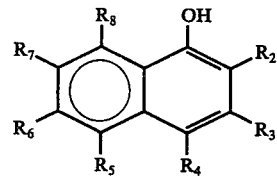

wherein $R_2$, $R_3$ and $R_4$ are hydrogen, an alkyl or an alkoxy group provided that either $R_2$ or $R_4$ is hydrogen and $R_5$, $R_6$, $R_7$ and $R_8$ are hydrogen, alkyl or alkoxy provided that tertiary alkyl groups or alkoxy groups are not attached to adjacent carbon atoms of the naphthalene molecule.

21. A method, as claimed in claim 20, wherein $R_2$ and $R_4$ are hydrogen.

22. A method, as claimed in claim 20, wherein the naphthol is 1-naphthol.

23. A method, as claimed in claim 1, wherein the phenol is 2,6-xylenol, the copper compound is cupric acetate, the surfactant is sodium lauryl sulfate and the alkaline material is an alkali metal carbonate or bicarbonate.

* * * * *